United States Patent [19]

Weber et al.

[11] Patent Number: 4,996,316

[45] Date of Patent: Feb. 26, 1991

[54] PROCESS FOR THE PREPARATION OF TERTIARY N, N-DIMETHYLAMINES

[75] Inventors: Jürgen Weber, Oberhausen; Detlef Kampmann, Bochum; Claus Kniep, Oberhausen, all of Fed. Rep. of Germany

[73] Assignee: Hoechst Aktiengesellschaft, Fed. Rep. of Germany

[21] Appl. No.: 281,801

[22] Filed: Dec. 24, 1988

[30] Foreign Application Priority Data

Dec. 9, 1987 [DE] Fed. Rep. of Germany .... 3741726

[51] Int. Cl.$^5$ ............................................. C07C 209/26
[52] U.S. Cl. ............................................ 544/1; 544/2; 544/3; 544/59; 544/63; 544/106; 544/162; 544/179; 544/180; 544/224; 546/26; 546/143; 546/159; 546/244; 546/264; 546/304; 548/122; 548/123; 548/124; 548/125; 548/130; 548/138; 548/161; 548/190; 548/212; 548/222; 548/233; 548/244; 548/245; 548/251; 548/255; 548/256; 548/257; 548/379; 548/337; 548/351; 548/372; 548/483; 548/557; 548/951; 548/953; 548/267.2; 549/9; 549/10; 549/11; 549/12; 549/21; 549/28; 549/38; 549/68; 549/88; 549/225; 549/243; 549/253; 549/321; 549/346; 549/371; 549/394; 549/404; 549/439; 549/467; 549/480; 549/505; 549/510; 564/308; 564/309; 564/374; 564/381; 564/382; 564/391; 564/398; 564/446; 564/462; 564/473

[58] Field of Search .................. 544/1, 2, 3, 59, 63, 544/106, 162, 179, 180, 224; 546/26, 143, 159, 244, 264, 304; 548/122, 123, 124, 125, 130, 138, 161, 190, 212, 222, 233, 244, 245, 251, 255, 256, 257, 266, 329, 337, 351, 372, 483, 557, 951, 953; 549/9–12, 21, 28, 38, 68, 88, 225, 243, 253, 321, 346, 371, 394, 404, 424, 439, 449, 467, 480, 505, 510; 564/308, 309, 374, 381, 382, 391, 398, 446, 462, 473

[56] References Cited

U.S. PATENT DOCUMENTS

| | | | |
|---|---|---|---|
| 2,373,705 | 4/1945 | Olin et al. | 564/446 |
| 2,809,995 | 10/1957 | Noeske et al. | 564/473 |
| 3,522,309 | 7/1970 | Kirby | 564/446 |
| 3,597,438 | 8/1971 | Brake | 564/398 |
| 4,190,601 | 2/1980 | Decker et al. | 564/473 |
| 4,207,260 | 6/1980 | Imai | 564/398 |
| 4,373,107 | 2/1983 | Tahara et al. | 564/473 |
| 4,757,144 | 7/1988 | Okabe et al. | 564/473 |
| 4,792,622 | 12/1988 | Yokota et al. | 564/473 |

FOREIGN PATENT DOCUMENTS

| | | | |
|---|---|---|---|
| 142868 | 5/1985 | European Pat. Off. . | |
| 436414 | 10/1935 | United Kingdom . | |
| 0716649 | 10/1954 | United Kingdom | 564/446 |

*Primary Examiner*—Glennon H. Hollrah
*Assistant Examiner*—Susan P. Treanor
*Attorney, Agent, or Firm*—Jordan B. Bierman

[57] ABSTRACT

A process for the preparation of tertiary N,N-dimethylamines by the reaction of primary amines, formaldehyde, and hydrogen under pressure and at elevated temperature in the presence of a nickel-containing hydrogenation catalyst in the liquid phase. The hydrogenation catalyst is suspended in a solvent, the nickel concentration is 0.1 to 10% by weight, based on the primary amine. The starting materials are separate from each other, brought to 80° to 150° C. and 1 to 15 MPa and fed into the catalyst suspension simultaneously with stirring and reacted in one step to form the tertiary N,N-dimethylamines.

60 Claims, No Drawings

PROCESS FOR THE PREPARATION OF TERTIARY N, N-DIMETHYLAMINES

The present invention relates to a process for the preparation of tertiary N,N-dimethylamines by the reaction of primary amines with formaldehyde and hydrogen in the presence of a hydrogenation catalyst in the liquid phase. Any monovalent or multivalent primary amines, as well as mixtures thereof, can be used as the amines. The reaction takes place at elevated temperature and generally requires an elevated pressure. It results in the complete replacement of all the hydrogen atoms located on the amine nitrogen atom by methyl groups, water being formed. This reaction is also termed hydrogenating N-methylation of amines.

BACKGROUND OF THE INVENTION

Tertiary amines are industrially significant compounds. They can serve as polymerization and curing catalysts for the production of epoxy and urethane-based plastics. Moreover, they are suitable as corrosion inhibitors and adsorption agents for synthesis gas scrubbing. This applies in particular to the easily prepared dimethyl derivatives.

The hydrogenating methylation of primary amines with formaldehyde and hydrogen is an important synthesis route to the preparation of methylated amines. A summary of this process is to be found in Houben-Weyl, Methoden der organischen Chemie; Vol. XI/1, pages 641 to 643, 4th edition (1957).

According to DE-OS 19 32 422 the reaction can be performed using conventional fixed-bed catalysts in liquid phase. Prior application DE 37 21 539 describes a modified process. Here, the starting materials (amine, formaldehyde and hydrogen) are heated separately to a specified temperature and then mixed in the presence of a fixed-bed catalyst. The starting materials, in particular the formaldehyde, are to contain a reduced amount of water. The fixed catalysts are placed in tubular reactors which can withstand the necessary high pressures.

However, it is also possible to dispense with the use of complicated high-pressure tubular reactors and to perform the reaction, for example, in vessels with stirring or loop reactors. In this case, the hydrogenating N-methylation is conducted with the aid of a suspended hydrogenation catalyst. This process is also called the suspension method; the present invention relates to this process variation.

After prolonged use, the hydrogenation catalysts decompose to an increasing extent. The resultant fine-grained particles are undesirable as they make the separation of the suspended catalyst after reaction more difficult. Normally, the suspended catalyst is removed by sedimentation, centrifugation, and/or filtration. The finer the catalyst particles are, the more difficult it is to remove them from the reaction mixture. A smaller particle size means a reduction in the rate of sedimentation, and also has a negative effect on centrifugation. If filtration is employed to separate the catalyst, the particularly small particles quickly block the filtration unit by clogging the filter pores. This causes an increase in pressure in the apparatus with the result that filtration has to be interrupted to clean the filter.

The presence of formic acid, which probably forms from formaldehyde through the Cannizzaro reaction, is also undesirable. It removes a corresponding amount of amine from the reaction in the form of a salt. In addition, the free acid and the amine salt promote corrosion in the reactor system.

Further disruptive side reactions are a result of the polymerization of formaldehyde with itself and the polycondensation between the amine and the formaldehyde to hexahydrotriazines or, in the case of multivalent amines, higher molecular compounds. The formation of polymeric substances produces a reduction in the catalyst activity owing to caking of the suspended catalyst and can even lead to the reactor being blocked. The unavoidable consequence is that the catalyst has to be changed.

The EP-A 0 142 868 recommends, for the N-alkylation of amines, the use of special hydrogenation catalysts which contain at least one of the elements Co, Ni, Ru, Rh, Pd and Pt on carbon as a carrier. The catalyst is suspended in the amine and the carbonyl compound added continuously. Aluminum oxide, silicon dioxide, and siliceous earth are undesirable as carriers for the hydrogenation catalysts since they do not ensure good distribution of the catalyst in the reaction system. Although metal catalysts without carriers, such as Raney nickel, Raney cobalt, palladium black, and platinum black are very active, they do not produce good results, as comparative tests have shown.

The teachings of ES 538 216 are comparable. While Pd and Pt-containing catalysts give good results on activated carbon, Raney nickel and a standard nickel carrier catalyst produce highly unfavorable results in the N-methylation of primary amines. This has been confirmed in comparative tests.

As can be seen from the preceding statements, the successful use of nickel-containing catalysts for the reaction of primary amines with formaldehyde and hydrogen is limited to special nickel-activated carbon carrier catalysts.

DETAILED DESCRIPTION OF THE PRESENT INVENTION

Surprisingly, it has been found that the N-methylation of primary amines using any nickel-containing catalysts can be performed without any appreciable reduction in conversion and selectivity. With nearly quantitative conversion, the reaction produces distillative yields of 90% and more based on the amine used.

The present process for the preparation of tertiary N,N-dimethylamine comprises reacting one or more primary amines, formaldehyde, and hydrogen at elevated temperatures and pressures in the presence of a nickel-containing hydrogenation catalyst. The catalyst should be in liquid form; e.g. suspended in a solvent. Moreover, the concentration of nickel is between 0.1% and 10% by weight based on the total primary amine and the catalyst should contain at least 10% nickel by weight.

It is a feature of the present invention that the primary amine and the formaldehyde are separately brought to and maintained at 80° to 150° C. and 1 to 15 MPa. It is preferred that all three of the reactants be kept separate and individually brought to the foregoing conditions; thereafter, they are introduced into the reaction chamber substantially simultaneously in the presence of the catalyst. While it is permissible to pre-mix the hydrogen with either of the other two reactants, the formaldehyde and primary amine must not be allowed to come into contact outside of the presence of the catalyst.

The reaction is carried out in known manner, particularly at a temperature of 90° to 130° C. A preferred temperature range is 90° to 125° C., most desirably, from 100° to 120° C. The more advantageous pressure range is 1.5 to 12 MPa, preferably 3 to 10 MPa. Most preferable is 5 to 8 MPa.

The catalyst can be selected from a variety of commercially available products of this type. However, as previously indicated, it should contain at least 10% nickel by weight. Such catalysts having over 20% nickel are even more suitable. In fact, catalyst having 20% to 80% nickel, preferably 40% to 70% nickel, have been found even more desirable. Most useful are catalysts containing 50% to 65%. In many cases, catalysts of this type containing a minimum of 40% by weight of nickel are used.

The catalysts need not be on carriers, although the presence of a suitable carrier is advantageous. Of course, they may contain the usual additives and/or promoters; e.g. alkaline earth oxides, $SiO_2$, $Al_2O_3$, $MnO_2$, $Cr_2O_3$, or mixtures thereof. If carriers are to be used, $Al_2O_3$, $SiO_2$, siliceous earth, silica gel, activated carbon, pumice stone, and the like are quite suitable. It has been found that $Al_2O_3$, $SiO_2$, siliceous earth, and silica gel are more suitable than the others, while $SiO_2$, siliceous earth, and silica gel are most preferred. Mixtures of these carriers are also suitable.

Insofar as the primary amines are concerned, there are no particular limitations. Any such amine having one or more primary amine groups is satisfactory. These include monovalent and multivalent amines, as well as aliphatic, cycloaliphatic, araliphatic, aromatic, and heterocyclic amines, and mixtures thereof.

Amines containing a total of 1 to 40 carbon atoms are worthy of particular mention. The substituents can be branched or straight chain alkyl groups having 1 to 24 carbon atoms, substituted or unsubstituted cycloalkyl groups having 5 to 20 carbon atoms, substituted or unsubstituted aromatic groups having 6 to 20 carbon atoms, or heterocyclic groups having 4 to 20 carbon atoms. In the last case, the hetero atom is advantageously oxygen, sulfur, and/or nitrogen. Mixtures of the foregoing are also suitable.

Examples of primary aliphatic amines are: methylamine, ehtylamine, propylamine, n- and i-butylamine, 3-methylbutylamine, n-pentylamine- 2-methylpentylamine, n-hexylamine, n- and i-heptylamine, n- and i-octylamine, n- and i-nonylamine, n- and i-decylamine, n- and i-undecylamine, 2-methylundecylamine, n-dodecylamine, n- and i-tridecylamine, n- and i-hexadecylamine, stearylamine, cerylamine, ethylenediamine, 1,3-diaminopropane, 1,4-diaminobutane, 1,6-diaminohexane (hexamethylenediamine-1,6) $\omega,\omega'$-polyalkylenediamines, and aminoalcohols such as ethanolamine, propanolamine, and diglycolamine.

The following are examples of cycloaliphatic amines useful in the present invention; cyclopentylamine, cyclohexylamine, and tricyclodecanamine. The ring system can have substituents, particularly alkyl groups. Useful araliphatic amines are benzylamine, alpha- and beta-phenylethylamine, and phenylpropylamine. Aniline, toluidine, benzidine (4.4'-diaminodiphenyl), phenylene diamine, and substituted and unsubstituted naphthylamines are aromatic amines which are operable in the present invention. The process according to the invention has proven particularly successful in the N-methylation of straight and/or branched chain primary aliphatic amines.

As their number of carbon atoms increases, primary aliphatic amines tend to transalkylate in the presence of nickel-containing hydrogenation catalysts to form correspondingly substituted dialkylamines and trialkylamines. When the process according to the invention is employed, however, these undesirable transfers of an alkyl group from one amine nitrogen atom to another do not occur. Thus, this procedure is admirably suited for the reaction of primary aliphatic amines having 4 to 24 carbon atoms. In particular 6 to 20 carbons and, most preferably, 8 to 16 carbon atoms may be used.

The nickel-containing catalyst can be in any form; e.g. lumps, filaments, tablets, pellets, granules, etc. Also, it can be used in crushed form or as a powder. The grains should be neither too fine nor too coarse. Coarse catalyst particles are undesirable because they have too small a surface area to adequately catalyze the reaction. On the other hand, fine-grained catalysts, although highly reactive due to their large surface area, are separated only with great difficulty by sedimentation, centrifugation, or filtration. The person of ordinary skill will know how to properly select the catalyst particle size. The removal of nickel-containing catalysts after the reaction has been completed is necessary in order to avoid undesirable side reactions during purification. During distillation, even minor amounts of nickel lead to rearrangements and transalkylations. The by-products thus formed contaminate the desired tertiary N,N-dimethylamine.

Before the reaction begins, the nickel-containing hydrogenation catalyst is suspended in a solvent. This solvent should be inert to the reaction taking place; i.e. it must not interfere with the N-methylation. Suitable solvents are the reaction product itself; aliphatic, cycloaliphatic, aromatic hydrocarbons, ether, alcohols, and mixtures thereof. In many cases cyclic ethers and/or aliphatic alcohols have particularly proven their worth. Tetrahydrofuran, dioxane, and aliphatic alcohols having 1 to 6 carbon atoms are desirable. Methanol, ethanol, propanol, i-propanol, n-butanol, and/or i-butanol have proven particularly successful. In view of their good solubility in water, methanol, ethanol, and/or propanols are strongly recommended. Methanol and/or ethanol, preferably methanol have been found most suitable The solvent is selected depending on the primary amine to be reacted. Amines with a relatively high molecular weight require solvents of low polarity; e.g. benzene, toluene, xylene, and mixtures thereof. To adjust to the required polarity, it may be necessary to mix non-polar solvents with polar solvents.

When primary amines are reacted with formaldehyde and hydrogen, water is formed. Apart from this reaction water, water also enters the reaction with the feed materials, in particular with the formaldehyde. It is recommended that the water content be limited. At the end of the reaction, it should be a maximum of 35% of the total reaction mixture. It is more desirable to keep the content below 25%, preferably below 15%, by weight. If there is too much water, it can lead to the formation of a heterogeneous water phase and also damage the nickel-containing catalyst.

If a heterogeneously water phase is formed, it will settle to the bottom of the reactor and prevent the reaction from taking place, at least in the area of the catalyst which it surrounds. This part of the catalyst is no longer available for catalytic effect.

Too high a water content, particularly over an extended period of time, impairs the catalyst activity and reduces both the conversion and the selectivity of the reaction. Moreover, rapid decomposition of the catalyst is promoted. This applies to a great extent to a number of carrier catalysts. Obviously, the water attacks the carrier material and quickly reduces its life. Rapid decomposition of the suspended catalyst is disadvantageous owing to the poor separability of fine-grained catalyst particles.

The water in the reaction mixture can be limited by the type and quantity of solvent. The formaldehyde can contain about 60% by weight and more of water. Solvents which can dissolve water to a limited or high degree help prevent the formation of a heterogeneous water phase. They are advantageously present in an amount of at least 5% by volume, based on the volume of all the liquid starting materials; for economic reasons, the amount should be limited to 50% by volume.

In many cases, adding 5% to 40%, in particular 10% to 30%, most preferably 15% to 25% by volume of solvent based on the volume of all the liquid starting materials, is sufficient. If less reaction water forms per volume unit of amine, it is sufficient to add 5 to 20% by volume; if more reaction water is released per volume unit, 10% to 30% or 15% to 35% by volume are recommended, all based on the volume of all the liquid starting materials. At least some of the solvent is placed in the reactor at the beginning along with the nickel-containing hydrogenation catalyst. More can be added to the reaction with the starting materials, preferably the formaldehyde. The solvent can also be added to the reaction with the amine. This is especially recommended with pasty or solid primary amines of higher molecular weight.

The use of low-water, solvent-containing formaldehyde has proven particularly successful. Such solutions consist of formaldehyde, 5% to 15% by weight of water and 25% to 55% by weight of a water scavenger such as an aliphatic alcohol, especially methanol. The preferred ranges are 7% to 12% water and 30% to 40% alcohol. A solution containing about 55% by weight of formaldehyde, about 10% by weight of water, and about 35% by weight of methanol is well suited. A product with this composition is commercially available.

Normally the reaction is performed in a pressure-tight vessel. The mixing can be performed by circulating the suspended hydrogenation catalyst and/or by stirring. In many cases, a conventional vessel equipped with a stirrer can be used. The reaction can be performed as a continuous or batch process; however, it is particularly suitable for batch type operation.

The optionally crushed, nickel-containing hydrogenation catalyst is placed in the pressure vessel together with the solvent and suspended by mixing. The suspension is heated to 80° to 150° C. and a pressure of 1 to 15 MPa is attained by adding hydrogen. A major feature of the invention is that the starting materials are introduced separately and simultaneously into the catalyst suspension with mixing. This means that the amine, formaldehyde, and hydrogen are preferably fed through their own separate lines into the reaction zone where the suspended catalyst is located. It is also possible to add the hydrogen to the reaction in a mixture with either the amine or the formaldehyde. It is furthermore possible to distribute the hydrogen between the amine and formaldehyde. However, the amine and the formaldehyde may only come into contact with each other in the presence of the suspended catalyst.

It is possible to have the lines of two or all three starting materials terminating in the zone of the suspended catalyst. The arrangement of the lines to be selected depends on the amounts of material, the geometry of the reaction zone, and the required flow conditions. If the throughput of the substances per time unit is to be substantial, it is recommended that several lines per starting material be provided. Should the flow conditions not ensure adequate mixing of the reactants in the catalyst zone, the use of additional distributing equipment is useful. These distributors can, for example, be ring showers or shower heads mounted at the end of a line. However, other distribution systems such as jets, frits, pipe bundles, etc. can also be used.

In accordance with a special embodiment of the invention, the primary amine and formaldehyde are introduced into the catalyst suspension through two separate dip pipes. The hydrogen can be introduced either through another dip pipe into the reaction zone or through a pipe nozzle into the gas chamber located above the suspension. The reaction conditions, especially the pressure, temperature, and duration of reaction, also depend to a certain extent on the type of primary amine and the suspended hydrogenation catalyst. Amines of low thermal stability are reacted at 80° to 100° C., amines of medium reactivity at 100° to 120° C., and those of low reactivity at 120° to 150° C. Nickel-containing catalysts with high activity permit a reaction at relatively low temperatures, whereas catalysts with medium activity require higher temperatures.

The activity of the catalyst drops as a function of the length of its use. Catalysts which have been re-used several times in hudrogenating N-methylation require ever higher reaction temperatures in the course of time to ensure an optimum synthesis process. Even originally very active catalysts can require reaction temperatures of 140° C. and more under these circumstances.

The amount of formaldehyde required depends on the number of hydrogen atoms on the primary amine nitrogen, 1 to 2, in particular 1 to 1.5, preferably 1.1 to 1.25, moles of formaldehyde are used per gram atom of hydrogen to be substituted. As a rule, a stoichiometric excess of 5 to 30 mol % of formaldehyde will have a positive effect on the reaction.

The amount of hydrogen required is governed by the stoichiometry of the reaction. Normally, the hydrogen is added in an amount which ensures that a specified pressure is maintained. Excess hydrogen used can be separated from the reaction and fed back into the reaction process.

The primary amine and formaldehyde are added separately but simultaneously. This must not take place too quickly due to the risk of undesirable by-products being formed. Slightly too rapid dosing of amine and formaldehyde can be corrected by an after-reaction without appreciable amounts of by-products being formed. In most cases, a time of 0.5 to 2 hours is sufficient for this purpose. However, too slow addition can promote the formation of high-boiling substances.

The charging rate should be the same for all feed materials, especially for the primary amine and the formaldehyde. It depends on various factors such as the size of the batch, reactivity of the amine, type of amine, reactor geometry, type of catalyst, nickel concentration, intensity of mixing, pressure and temperature. It is to be adapted to the prevailing conditions and, if necessary, can readily be determined empirically by the person of ordinary skill. The consumption of hydrogen per unit time is a useful aid to check the progress of the reaction. When no more hydrogen is consumed, the reaction is completed.

The following examples illustrate the invention without limiting it.

EXAMPLE 1

The reactor vessel consists of a 2 liter autoclave, equipped with a stirrer, which has 2 dip pipes in addition to an inlet for the supply of hydrogen.

5 g of a pulverized nickel catalyst (containing about 50% to 53% by weight Ni and roughly 25 to 30% by weight of diatomaceous earth as carrier; (a proprietary product of Hoechst AG: RCH Ni 52/35) and 100 g of methanol are poured in the vessel. The pulverized catalyst is suspended with stirring and the desired conditions (10 MPa hydrogen pressure; 120° C.) are established.

After the desired conditions are reached, 258 g (2 moles) of n-octylamine and 275 g of a formaldehyde solution (approximately 55% by weight formaldehyde, 10% by weight water, and 35% by weight methanol)—corresponding to 5 moles of formaldehhyde—are simultaneously pumped into the catalyst suspension via the two dip pipes over a period of 2 hours.

EXAMPLES 2 TO 4

The procedure of Example 1 is followed except that the pumping time for the feed materials n-octylamine and formaldehyde is 90 minutes in Example 2, 60 minutes in Example 3, and 30 minutes in Example 4.

EXAMPLE 5

This procedure of Example 1 is followed except that 5 g of a different pulverized nickel catalyst having approximately 55% by weight nickel on diatomaceous earth as the carrier (a proprietary product of Hoechst AG:RCH Ni 55/5) is used.

COMPARATIVE TEST A

Using the reactor vessel described in Example 1, 258 g (2 moles) of N-octylamine and 5 g of the nickel catalyst is used in Example 1 are charged therein. No methanol is included. The pulverized catalyst is suspended with stirring and the desired conditions (10 MPa hydrogen pressure, 120° C.) are established.

After the desired conditions are reached, 275 g of the formaldehyde solution used in Example 1—corresponding to 5 moles of formaldehyde—are pumped in over a period of 2 hours. The reaction product is in 2 phases, the lower (aqueous) phase consisting of 98% by weight of water and 2% by weight of N,N-dimethyl-n-octylamine. The composition of the organic (upper) phase is shown in Table 1 under A. A comparison with Example 1 shows a clear deterioration in the yield of the desired product.

In the following Table 1, the results of the gas chromatographic analysis (sampled directly after end of the pumping process) are given for Examples 1 to 5 and Comparative Test A. Table 2 contains the results of Examples 2 to 5, in each case after 1 hour after-reaction.

TABLE 1

| Composition* | Example | | | | | |
|---|---|---|---|---|---|---|
| | 1 | 2 | 3 | 4 | 5 | A |
| n-octylamine | — | <0.1 | <0.1 | <0.1 | — | <0.1 |
| N-methyl-n-octylamine | | 0.2 | 0.9 | 1.1 | 2.3 | 1.1 |
| N,N-dimethyl-n-octylamine | 93.1 | 93.3 | 96.2 | 98.1 | 96.7 | 78.26 |
| N,N-dioctyl-methylamine | 2.5 | 4.6 | 1.0 | — | 0.3 | 15.9 |

*all figures in % by weight; H₂O and methanol excluded from calculation.

TABLE 2

| Composition* | Example | | | |
|---|---|---|---|---|
| | 2 | 3 | 4 | 5 |
| n-octylamine | — | — | — | — |
| N-methyl-n-octylamine | 0.2 | 0.5 | 0.6 | 1.1 |
| N,N-dimethyl-n-octylamine | 93.7 | 96.7 | 98.4 | 97.8 |
| N,N-dioctyl-methylamine | 4.7 | 0.7 | — | 0.1 |

*all figures in % by weight; H₂O and methanol excluded from calculation.

EXAMPLE 6

The procedure is analogous to Example 1.

After the desired conditions are reached, 185 g (1 mole) of n-dodecylamine and 138 g of the formaldehyde solution used in Example 1—corresponding to 2.5 moles of formaldehyde—are pumped in through the two dip pipes separately but simultaneously over a period of 2 hours. The reaction mixture contains 0.6% by weight of N-methyl-n-dodecylamine, 93.6% by weight of N,N-dimethyl-n-dodecylamine and 0.6 by weight of N,N-didodecylmethylamine by gas chromotography analysis (H₂O and methanol excluded from calculation).

COMPARATIVE TEST B

The procedure of Comparative Test A is followed except that, instead of n-ocytlamine, 185 g (1 mole) of n-dodecylamine and 3 g of the nickel catalyst used in Example 1 are charged into the reactor. 138 g of the formaldehyde solution is added as in Comparative Test A.

The reaction mixture is 2 phases, the lower (aqueous) phase consisting of 89.7% by weight of water and 10.3% by weight of methanol. The upper (organic) phase contains 0.9% by weight of N-methyl-n-dodecylamine, 80.3% by weight of N,N-dimethyl-n-dodecylamine and 16.7% by weight of N,N-didodecylmethylamine by gas chromatography analysis (H₂O and methanol excluded from the calculation).

A comparison with Example 6 shows a clear deterioration in the yield of the desired product.

What we claim is:

1. A process for the preparation of tertiary N,N-dimethylamine comprising a reaction among a mixture of at least one primary amine, formaldehyde, and hydrogen as starting materials at elevated temperature and pressure in the presence of a hydrogenation catalyst consisting essentially of nickel as a catalytically active metal, said catalyst being in a liquid form suspended in a solvent, the concentration of said nickel being 0.1% to 10% by weight based on said primary amine, said catalyst containing at least 10% nickel by weight, said primary amine and said formaldehyde being separately and simultaneously supplied to said reaction at 80° to 150 ° C. and under a pressure of 1 to 15 MPa, whereby said tertiary N,N-dimethylamine is formed in a single reaction step.

2. The process of claim 1 wherein each of said starting materials is separately and simultaneously supplied to said reaction at 80° to 150° C. and under a pressure of 1 to 15 MPa.

3. The process of claim 1 wherein said primary amine is multivalent.

4. The process of claim 1 wherein said primary amine is taken from the class consisting of aliphatic amines, cycloaliphatic amines, araliphatic amines, aromatic amines, heterocyclic amines having 4 to 20 carbon atoms and containing at least one atom of oxygen, sulfur, or nitrogen, and mixtures thereof.

5. The process of claim 1 wherein said primary amine has 1 to 40 carbon atoms.

6. The process of claim 4 wherein said primary amine has a substituent which is straight and/or branched chain alkyl having 1 to 14 carbons, substituted and/or unsubstituted cycloalkyl having 5 to 20 carbon atoms, aromatic having 6 to 20 carbons, and/or heterocyclic having 4 to 20 carbons which may contain oxygen, sulfur, and/or nitrogen as a hetero atom.

7. The process of claim 1 wherein said primary amine is methylamine, ethylamine, n and i-butylamine, 3-methylbutylamine, n-pentylamine, 2-methylpentylamine, n-hexylamine, n and i-heptylamine, n and i-octylamine, n and i-nonylamine, n and i-decylamine, n and i-undecylamine, 2-methylundecylamine, n-dodecylamine, n and i-tridecylamine, n and i-hexadecylamine, stearylamine, ceryl amine, ethylenediamine, 1,3-diaminopropane, 1,4-diaminobutane, 1,6-diaminohexane, 1,4-diaminobutane, 1,6-diaminohexane, (λ), (λ)'-polyalkylenedamines, aminoalcohols, or mixtures thereof.

8. The process of claim 7 wherein said alcohols are ethanolamine, propanolamine, and diglycolamine.

9. The process of claim 4 wherein said primary amine is cyclopentylamine, cyclohexylamine, tricyclodecanamine, and mixtures thereof.

10. The process of claim 9 wherein said primary amine has at least one substituent.

11. The process of claim 10 wherein said substituent is alkyl.

12. The process of claim 4 wherein said primary amine is benzylamine, α-phenylethylamine, β-phenylethylamine, phenylpropylamine, or mixtures thereof.

13. The process of claim 4 wherein said primary amine is aniline, toluidine, benzidine, phenylene diamine, naphthylamine, and mixtures thereof.

14. The process of claim 6 wherein said primary amine is at least one straight or branched chain aliphatic amine.

15. The process of claim 6 wherein said primary amine is at least one straight or branched chain aliphatic amine having 4 to 24 carbons.

16. The process of claim 15 wherein said primary amine has 6 to 20 carbons.

17. The process of claim 16 wherein said primary amine has 8 to 16 carbons.

18. The process of claim 1 wherein said temperature is 90° to 130° C.

19. The process of claim 18 wherein said temperature is 95° to 125° C.

20. The process of claim 19 wherein said temperature is 100° to 120° C.

21. The process of claim 1 wherein said pressure is 1.5 to 12 MPa.

22. The process of claim 21 wherein said pressure is 3 to 10 MPa.

23. The process of claim 22 wherein said pressure is 5 to 8 MPa.

24. The process of claim 1 wherein said catalyst contains at least 20% nickel by weight.

25. The process of claim 24 wherein said catalyst contains 20% to 80% nickel by weight.

26. The process of claim 25 wherein said catalyst contains 40% to 70% nickel by weight.

27. The process of claim 26 wherein said catalyst contains 50% to 65% nickel by weight.

28. The process of claim 26 wherein said catalyst contains at least 40% nickel by weight.

29. The process of claim 1 wherein said catalyst contains at least one alkaline earth oxide, $SiO_2$, $Al_2O_3$, $MNO_2$, and/or $Cr_2O_3$.

30. The process of claim 1 wherein a carrier for said catalyst is present.

31. The process of claim 1 wherein said carrier is $Al_2O_3$, $SiO_2$, siliceous earth, silica gel, activated carbon, pumice stone, or mixtures thereof.

32. The process of claim 31 wherein said carrier is $Al_2O_3$, $SiO_2$, siliceous earth, silica gel, or mixtures thereof.

33. The process of claim 32 wherein said carrier is $SiO_2$, siliceous earth, silica gel, or mixtures thereof.

34. The process of claim 1 wherein said solvent is taken from the class consisting of reaction products of said mixture, aliphatic hydrocarbons, cycloaliphatic hydrocarbons, aromatic hydrocarbons, ethers, alcohols, and mixtures thereof.

35. The process of claim 34 wherein said solvent is taken from the class consisting of cyclic ethers, aliphatic alcohols, and mixtures thereof.

36. The process of claim 34 wherein said solvent is taken from the class consisting of tetrahydrofuran, dioxane, aliphatic alcohols having 1 to 6 carbons, and mixtures thereof.

37. The process of claim 36 wherein said solvent is methanol, ethanol, propanol, and mixtures thereof.

38. The process of claim 37 wherein said solvent is methanol or ethanol.

39. The process of claim 37 wherein said solvent is methanol.

40. The process of claim 1 wherein, after carrying out said reaction to form a reaction mixture, said reaction mixture contains a maximum of 35% water by weight.

41. The process of claim 40 wherein said maximum is 25% by weight.

42. The process of claim 41 wherein said maximum is 15% by weight.

43. The process of claim 1 wherein a water scavenger is present in said starting materials.

44. The process of claim 43 wherein said scavenger is present in an amount of at least 5% by volume based on all liquid starting materials.

45. The process of claim 44 wherein said amount is not more than 50% by volume.

46. The process of claim 45 wherein said amount is not more than 40% by volume.

47. The process of claim 46 wherein said amount is 10% to 30% by volume.

48. The process of claim 47 wherein said amount is 15% to 25% by volume.

49. The process of claim 45 wherein said amount is 5% to 20% by volume.

50. The process of claim 1 wherein said formaldehyde contains 5% to 15% water by weight and 25% to 55% aliphatic alcohol by weight.

51. The process of claim 50 wherein said formaldehyde contains 7% to 12% water by weight and 30% to 40% aliphatic alcohol by weight.

52. The process of claim 50 wherein said aliphtic alcohol is methanol.

53. The process of claim 52 wherein said formaldehyde contains 10% water by weight and 35% methanol by weight.

54. The process of claim 1 wherein there are 1 to 2 mols of formaldehyde per gram atom of hydrogen to be substituted.

55. The process of claim 54 wherein there are 1to 1.5 mols of formaldehyde per gram atom of hydrogen to be substituted.

56. The process of claim 55 wherein there are 1.1 to 1.25 mols of formaldehyde per gram atom of hydrogen to be substituted.

57. The process of claim 1 wherein said formaldehyde is present in a stoichiometric excess of 5 to 30 mol %.

58. The process of claim 1 wherein said nickel is present in an amount of 0.2% to 5% by weight based on said primary amine.

59. The process of claim 58 wherein said amount is 0.3% to 2.0% by weight.

60. The process of claim 59 wherein said amount is 0.6% to 1.3% by weight.

* * * * *